United States Patent [19]
Packard et al.

[11] Patent Number: 5,931,792
[45] Date of Patent: Aug. 3, 1999

[54] STETHOSCOPE CHESTPIECE

[75] Inventors: Thomas J. Packard; Joy A. Packard, both of St. Paul, Minn.

[73] Assignee: 3M Innovative Properties Company, St. Paul, Minn.

[21] Appl. No.: 08/965,262

[22] Filed: Nov. 6, 1997

[51] Int. Cl.$^6$ ....................................................... A61B 7/02
[52] U.S. Cl. ............................................ 600/528; 181/131
[58] Field of Search ............................ 600/528; 181/131, 181/137; 381/67; D24/134

[56] References Cited

U.S. PATENT DOCUMENTS

| | | |
|---|---|---|
| D. 208,125 | 7/1967 | Cefaly . |
| 2,505,124 | 4/1950 | Lepeschkin . |
| 2,513,827 | 7/1950 | Tynan . |
| 3,124,211 | 3/1964 | Cefaly .................................. 181/131 |
| 3,144,091 | 8/1964 | Bodenger ............................. 181/137 |
| 3,515,239 | 6/1970 | Machlup et al. .................... 181/137 |
| 3,587,776 | 6/1971 | Haiken ................................. 181/137 |
| 3,630,308 | 12/1971 | Ravin . |
| 4,212,689 | 7/1980 | Allen . |
| 4,440,258 | 4/1984 | Packard . |
| 4,770,270 | 9/1988 | Grimm . |
| 4,852,684 | 8/1989 | Packard . |
| 4,913,259 | 4/1990 | Packard . |
| 4,991,686 | 2/1991 | Allen ...................................... 181/131 |
| 5,111,904 | 5/1992 | Packard et al. . |
| 5,324,471 | 6/1994 | Packard et al. . |
| 5,380,182 | 1/1995 | Packard et al. . |
| 5,449,865 | 9/1995 | Desnick et al. . |

FOREIGN PATENT DOCUMENTS

| | | |
|---|---|---|
| 0 408 329 A2 | 1/1991 | European Pat. Off. . |
| 1514345 | 6/1969 | Germany . |
| WO 97/19639 | 6/1997 | WIPO . |

*Primary Examiner*—William E. Kamm
*Assistant Examiner*—George R. Evanisko
*Attorney, Agent, or Firm*—Gary L. Griswold; Eloise J. Maki; Jeffrey J. Hohenshell

[57] ABSTRACT

A stethoscope with a chestpiece which has two microphones oriented at a very obtuse angle to each other. The user of the stethoscope can switch from one microphone to the other with just a slight tilt of the hand. In preferred embodiments, no special action needs to be taken to activate the selected microphone as merely touching it to the patient's body selects it for activation.

10 Claims, 2 Drawing Sheets

STETHOSCOPE CHESTPIECE

TECHNICAL FIELD

The invention relates generally to acoustic stethoscopes, and more particularly to a stethoscope which may be readily and conveniently switched between two or more sound gathering components.

BACKGROUND

The stethoscope is one of the most recognizable tools in the physician's art. The heart, lungs, arteries, and joints emit sounds useful in diagnostic procedures. In order to be able to quickly focus on the particular sounds and to help the physician discriminate between normal and pathological sounds, the stethoscope art developed versatile instruments. For example, there are many stethoscopes which can either emphasize or de-emphasize particular frequency ranges depending on the physician's need of the moment.

One of the best known techniques for accomplishing this desirable versatility is to incorporate more than one sound collecting component or microphone into the chestpiece of the stethoscope. The two most conventional types of microphones are the diaphragm type, which has a thin, round disc of material defining a sound collecting surface, and the bell type, which as an open, concave shape. The lip of the bell defines a sound collecting surface that helps funnel acoustic energy toward passageways that carry sound to the ears. The bell type microphone conveys the lowest tones, such as the main "lub-dup" of the heartbeat. The diaphragm type microphones are most typically tuned to de-emphasize those lowest tones and to pass tones of slightly higher frequency. This helps the user of the stethoscope to more readily perceive the sounds typical of heart valve pathologies.

It is well known in the art to place a bell and diaphragm microphone on the chestpiece so as to increase the versatility of the stethoscope. It is also well known to employ microphones with sound collecting surfaces of different sizes. A large microphone is usually better at collecting the most acoustical energy, but a small microphone may be helpful if the patient is very small, or if the part of the body being contacted is bony, or if the site producing the sound must be localized very specifically, or if the site is located in a remote position that is difficult for the healthcare worker to reach.

When more than one microphone is present, the microphones should be conveniently arranged and the user should be able to rapidly choose between the microphones. U.S. Pat. No. 4,770,270 to Grimm discloses one bell type and one diaphragm type microphone placed on diametrically opposite sides of a chestpiece. A user switches between them by rotating a stem that connects the chestpiece to a binaural. It is also known to provide one bell type and one diaphragm type microphone on generally, but not diametrically, opposite sides of the chestpiece, and to arrange for selection between them. U.S. Pat. No. 2,505,124 to Lepeschkin; U.S. Pat. No. 3,630,308 to Ravin; and U.S. Pat. No. 4,212,368 to Allen disclose prior art arrangements. Two microphones can be in the same plane as shown in U.S. Pat. No. Des. 208,125 to Cefaly, or in perpendicular planes as shown in U.S. Pat. No. 2,513,827 to Tynan.

A limitation of all of these devices is the inconvenience involved in switching the orientation of the chestpiece in space to apply one microphone after another, and the inconvenience involved in switching between the active and inactive microphone. Coassigned U.S. Pat. No. 4,440,258 discloses a diaphragm mounted on a flexible surround within the microphone. The stethoscope can readily switch between one response and the other by slight adjustments in the pressure applied by the user's hand against the chestpiece in contact with the patient's body.

SUMMARY OF THE INVENTION

The present invention provides a stethoscope with a chestpiece having two microphones oriented at a very obtuse angle to each other. The user of the stethoscope can switch from one microphone to the other by merely slightly tilting his or her hand. In preferred embodiments, no special action needs to be taken in order to activate the selected microphone; as merely touching it to the patient's body selects it for activation. Preferably, the microphones are of different sizes.

The invention includes a stethoscope having a binaural and a chestpiece in acoustic communication with the binaural. The chestpiece has at least two microphones. The microphones preferably have a substantially planar skin contacting area. The microphones may be bell or diaphragm type microphones. In the present invention, the included angle between the planes defined by these skin contacting areas is greater than 90 degrees and less than 180 degrees. An angle of about 160 degrees has been found to be particularly suitable as it requires only a 20 degree adjustment on the user's part to shift from one microphone to another. Surprisingly, a twenty degree adjustment is just enough so that the user is not left uncertain as to which microphone is active.

While bell microphones or diaphragm microphones could be used with the present invention, the stethoscope preferably has two diaphragm-type microphones. The two skin contacting diaphragms are preferably both supported by a flexible surround. More preferably, the stethoscope has a single diaphragm support which provides the flexible surrounds for both diaphragms.

Each microphone is acoustically associated with an acoustical valve which opens to permit acoustical conduction between that microphone and the binaural when the skin contacting diaphragm of that microphone is in contact with a patient's body. The acoustical valve is normally closed but opens upon contact between the microphone and the patient's body. The valve preferably includes a seat, a sealing member adapted to sealingly contact the seat, a means such as a spring for biasing the sealing member against the seat, and an elongated probe attached to the sealing member and extending toward the skin contacting diaphragm. When a microphone is pressed against a patient's body, the skin contacting diaphragm deflects inward on the flexible surround that supports it. That inward deflection moves the elongated probe which in turn moves the sealing member away from the seat.

For some applications, and particularly when a small diameter microphone is to be provided, it has been found that a low mass/stiffness ratio can be desirable for one or more of the skin contacting diaphragms. A polymer/carbon fiber is preferred. Unwanted noise within the stethoscope caused by the contact with the user's hand can be minimized by including a main portion on the chestpiece which is composed of a rigid material and mounting at least one, and more preferably two, gripping surfaces on the main portion. These gripping surfaces are sized and shaped to be gripped by a human hand. The gripping surfaces are composed of a resilient polymeric material to absorb and dissipate the contact noises.

In the present application, the word "microphone" means an arrangement of structural components for gathering acoustical energy and conveying it to a sound transmitting passageway. In the present context, the word microphone describes elements that may be used in an electrically powered stethoscope and also elements that may be used in stethoscopes which do not rely on electrical power for operation.

In traditional stethoscopes the rim of the bell or the rim of the diaphragm defines a surface which is essentially a mathematical plane in space. While the structures define surfaces that are close to mathematical planes, the structures rarely define a perfect mathematical plane due to a variety of factors (e.g. stethoscope wear, production tolerance vagaries, etc.). As a result, the present application uses the phrase "substantially planar surface", or "essentially planar surface" to describe surfaces which approximate a plane.

The substantially planar surface provided by the rim of the bell or by the rim of the diaphragm is herein referred to as the skin contacting surface of the stethoscope. It should be noted, however, that the skin contacting surface need not be planar. The phrase "the included angle between the planes" means the angle between the two planes as measured through the main portion of the chestpiece.

BRIEF DESCRIPTION OF THE DRAWING

In the several figures of the attached drawing, like parts bear like reference numerals, and.

DETAILED DESCRIPTION OF A PREFERRED EMBODIMENT

Figure 1:
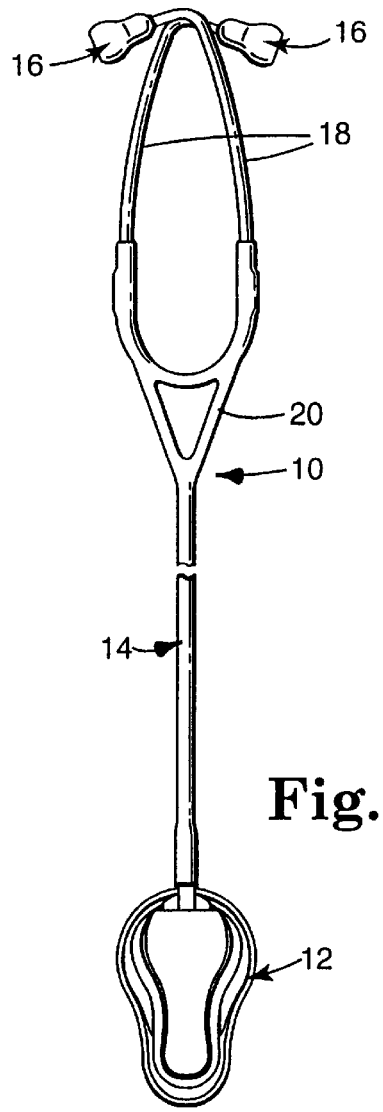
FIG. 1 is a plan view of a stethoscope according to the present invention.

FIG. 1 illustrates a stethoscope 10 according to the present invention. The stethoscope 10 includes a chestpiece 12 and a binaural 14. The word "binaural" means the combination of sound conveying tubing and headset normally attached to the chestpiece for conveying sound from the chestpiece to the user's ears. The binaural 14 typically has ear tips 16 on eartubes 18 which combine at a yoke section 20. These elements contain sound conveying passageways to transmit sound from the chestpiece 12 to the user's ears. The binaural and other elements of the stethoscope may be constructed in accordance with the teachings of U.S. Pat. Nos. 5,111,904; 5,380,182; and 5,324,471 to Packard et al. (each of which is hereby incorporated by reference). The ear tips are sized and shaped to engage the surfaces of the user's ears. The ear tips may comprise any suitable ear tips. Preferably, the ear tips comprise the soft ear tips disclosed in U.S. Pat. Nos. 4,852,684; 4,913,259 and 5,449,865 (the entire contents hereby incorporated by reference).

Figure 2:
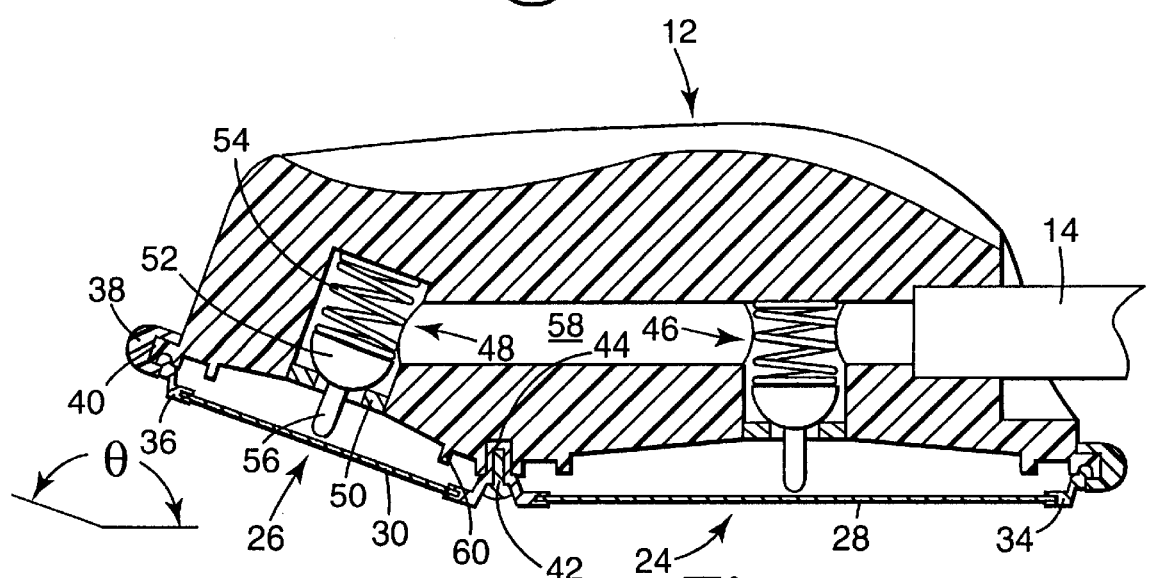
FIG. 2 is a cross-sectional view of the stethoscope chestpiece with portions of the stethoscope broken away to illustrate details.
Figure 3:
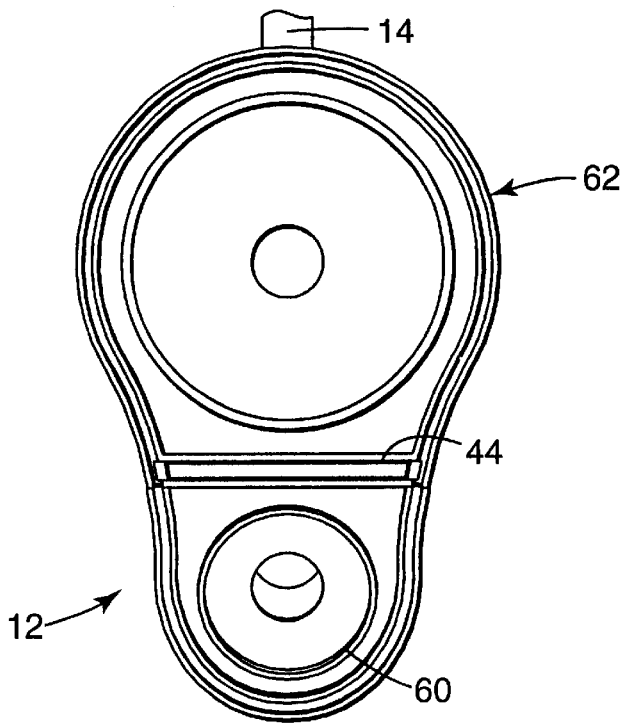
FIG. 3 is a bottom view of the stethoscope chestpiece with elements such as the diaphragm and diaphragm support omitted to emphasize other details.
Figures 4, 5:
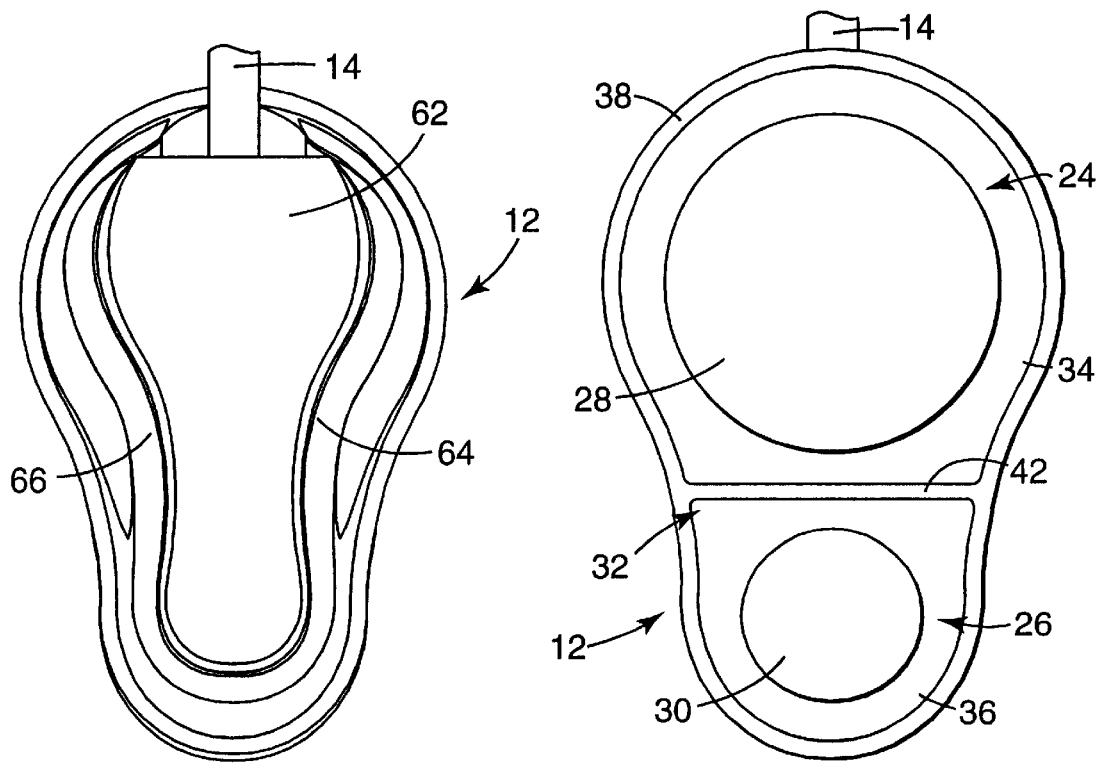
FIG. 4 is a top view of the stethoscope chestpiece of FIG. 3.
FIG. 5 is a bottom view of the stethoscope chestpiece according to the present invention showing a pair of diaphragms.

Referring to FIG. 2, the chestpiece has a first and a second microphone, 24 and 26 respectively. The microphones 24 and 26 include first and second diaphragms 28 and 30. Both diaphragms are preferably constructed from a thin, circular disk of material. Non-circular diaphragms could also be utilized. Preferably, the microphones comprise diaphragm type microphones. The diaphragm microphones may be constructed from a polymer/carbon fiber composite. For example, a microphone may be constructed from a 0.008 inch thick uni-carbon laminate part number ACO 0.008"/BT250E-1(+/−0.002"), available from Aerospace Composite Products of San Leandro, Calif. Such a material may have a tensile strength of 285 ksi with a modulus of 19 Msi, a compressive strengths of 245 ksi with a modulus of 18.5 Msi, a flexural strength of 260 ksi with a modulus of 19.2 Msi, and a short beam shear strength of 15 ksi.

A diaphragm support 32 is provided which provides a flexible surround 34 and 36 attached to and flexibly supporting diaphragms 28 and 30. A snap-on rim 38 grips the diaphragm support 32 around the periphery of the chestpiece 12.

Referring to FIG. 2, the included angle θ between the planes of diaphragms 28 and 30 is very obtuse. This angle should be greater than 90 degrees and less than 180 degrees, and is preferably between about 145 degrees and 170 degrees, and is most preferably between about 155 degrees and 165 degrees. In the illustrated embodiment the angle θ is about 160 degrees. Diaphragms 28 and 30 are flexibly supported by flexible surrounds 34 and 36. The surrounds 34 and 36 are part of diaphragm support 32. The diaphragm support 32 is held by a rim 38 which is snapped over a flange 40 on the periphery of the chestpiece 12. The diaphragm support 32 may include a bead or rib 42 which fits into a channel 44 in the chestpiece 12.

Microphones 24 and 26 each include an acoustical valve 46 and 48. Each acoustical valve 46 and 48 includes a seat 50, a sealing member 52 adapted to sealingly contact the seat 50, a spring 54 which serves as a means for biasing the sealing member 52 against the seat 50, and an elongated probe 56 attached to the sealing member 52 and extending toward the skin contacting diaphragm 28 or 30. For example, when diaphragm 30 of microphone 26 is pressed into contact with a patient's body, diaphragm 30 deflects inward on the flexible surround 36 that supports it. This inward deflection causes the elongated probe 56 to move, thereby moving the sealing member 52 away from the seat 50. This allows acoustical energy gathered by diaphragm 30 to enter sound conveying passageway 58. The sound can then travel from the passageway 58 to the binaural 14. If the diaphragm 30 is pressed sufficiently firmly against the patient's body, it will contact annular ring 60, which will cause the acoustical characteristics of microphone 26 to change. Specifically, such contact will cause the diaphragm 30 to attenuate lower sound frequencies. Additional details associated with diaphragms of this type can be found in coassigned U.S. Pat. No. 4,440,258 to Packard and U.S. patent application Ser. No. 08/904,384 filed Aug. 1, 1997 (attorney ref. no. 53586USA1A), the entire contents of each of which are hereby incorporated by reference. The stem 14 is used to connect the sound conveying passageway 58 in chestpiece 12 to the sound conveying passageway in the binaural 14.

The chestpiece 12 has a main portion 62 composed of a rigid material such as stainless steel. While other materials can be used, stainless steel provides a suitable mass for enhancing sound gathering ability. The chestpiece also has gripping surfaces 64 and 66 on the main portion 62 which are sized and shaped to be gripped by a human hand. These gripping surfaces 64 and 66 may be constructed from a resilient polymeric material mounted on the stainless steel. Mounting the gripping surfaces 64 and 66 on the rest of the stainless steel chestpiece reduces extraneous noise during the ordinary use of the stethoscope 10. In particular, a thermoplastic rubber, commercially available as Santoprene, from Advanced Elastomer Systems of Akron, Ohio, is considered particularly suitable.

Various modifications and alterations of the present invention will be apparent to those skilled in the art without departing from the scope and spirit of this invention, and it should be understood that this invention is not limited to the illustrative embodiments set forth herein.

What is claimed is:

1. A stethoscope, comprising:

a binaural and a chestpiece in acoustic communication with the binaural, the chestpiece comprising at least two microphones, each microphone having a skin contacting area defining a substantially planar surface, the microphones being positioned on the chestpiece such that the included angle between the substantially planar surfaces is greater than 90 degrees and less than 180 degrees.

2. A stethoscope according to claim 1 wherein the included angle is between about 145 degrees and 170 degrees.

3. A stethoscope according to claim 2 wherein the included angle is between about 155 degrees and 165 degrees.

4. A stethoscope according to claim 1 wherein each microphone comprises a diaphragm adapted to contact the skin.

5. A stethoscope according to claim 4 wherein each diaphragm is supported by a flexible surround.

6. A stethoscope according to claim 5 further comprising a single diaphragm support wherein each of the flexible surrounds is a part of the diaphragm support.

7. A stethoscope according to claim 5 wherein each microphone further comprises an acoustical valve which opens to permit acoustical conduction between that microphone and the binaural when the diaphragm of that microphone is in contact with a patient's body.

8. A stethoscope according to claim 7 wherein each acoustical valve comprises a seat, a sealing member adapted to sealingly contact the seat, a means for biasing the sealing member against the seat, and an elongated probe attached to the sealing member and extending toward the diaphragm whereby when the diaphragm of that microphone is in contact with a patient's body, the diaphragm deflects inward on the flexible surround that supports it, moving the elongated probe, and moving the sealing member away from the seat.

9. A stethoscope according to claim 4 wherein at least one of the diaphragms is composed of a polymer/carbon fiber composite.

10. A stethoscope according to claim 1 wherein the external surface of the chestpiece comprises a main portion composed of a rigid material, and at least one gripping surface mounted on the main portion, the gripping surface being sized and shaped to be gripped by a human hand, the gripping surface being composed of a resilient polymeric material.

* * * * *